US012568993B2

(12) United States Patent (10) Patent No.: US 12,568,993 B2
Parekh et al. (45) Date of Patent: Mar. 10, 2026

(54) SHELF-STABLE NITROGENOUS ORGANIC ACID COMPOSITIONS

(71) Applicant: GLANBIA DAIRY NUTRITION LIMITED, Kilkenny (IE)

(72) Inventors: Gaurav Parekh, Twin Falls, ID (US); Brent L. Petersen, Twin Falls, ID (US)

(73) Assignee: GLANBIA DAIRY NUTRITION LIMITED, Kilkenny (IE)

( * ) Notice: Subject to any disclaimer, the term of this patent is extended or adjusted under 35 U.S.C. 154(b) by 64 days.

(21) Appl. No.: 16/164,762

(22) Filed: Oct. 18, 2018

(65) Prior Publication Data

US 2019/0230960 A1 Aug. 1, 2019

Related U.S. Application Data

(60) Provisional application No. 62/726,421, filed on Sep. 3, 2018, provisional application No. 62/573,995, filed on Oct. 18, 2017.

(51) Int. Cl.
| | |
|---|---|
| *A23L 2/38* | (2021.01) |
| *A23L 2/39* | (2006.01) |
| *A23L 2/66* | (2006.01) |
| *A23L 2/68* | (2006.01) |
| *A23L 29/238* | (2016.01) |

(Continued)

(52) U.S. Cl.
CPC .................. *A23L 2/38* (2013.01); *A23L 2/39* (2013.01); *A23L 2/66* (2013.01); *A23L 2/68* (2013.01); *A23L 29/238* (2016.08); *A23L 33/175* (2016.08); *A61K 9/0095* (2013.01); *A61K 9/107* (2013.01); *A61K 47/24* (2013.01);

*A61K 47/36* (2013.01); *A61K 47/40* (2013.01); *A23V 2002/00* (2013.01); *A23V 2250/1842* (2013.01); *A23V 2250/306* (2013.01); *A23V 2250/5112* (2013.01); *A23V 2250/5114* (2013.01); *A23V 2300/10* (2013.01); *A23V 2300/26* (2013.01)

(58) Field of Classification Search
CPC .................................................. A23L 33/175
See application file for complete search history.

(56) References Cited

U.S. PATENT DOCUMENTS

| | | | | |
|---|---|---|---|---|
| 4,734,401 | A | * 3/1988 | Blouin | ..................... A61K 9/14 426/443 |
| 5,929,051 | A | * 7/1999 | Ni | ........................... C12P 19/04 514/54 |

(Continued)

FOREIGN PATENT DOCUMENTS

| | | |
|---|---|---|
| CN | 101536993 A | 9/2009 |
| CN | 102908337 A | 2/2013 |

(Continued)

OTHER PUBLICATIONS

Caffall et al., "The structure, function and biosynthesis of plant cell wall pectic polysaccharides", Carbohydrate Research 344 (2009) 1879-1900. (Year: 2009).*

(Continued)

*Primary Examiner* — Stephanie A Kohler
(74) *Attorney, Agent, or Firm* — Viksnins Harris Padys Malen LLP

(57) ABSTRACT

Disclosed is a method for making shelf-stable nitrogenous organic acid (e.g., creatine) ingredients for products such as nutritional bars, liquids, and/or powders.

13 Claims, 1 Drawing Sheet

(51) Int. Cl.

| | | |
|---|---|---|
| *A23L 33/175* | (2016.01) | |
| *A61K 9/00* | (2006.01) | |
| *A61K 9/107* | (2006.01) | |
| *A61K 47/24* | (2006.01) | |
| *A61K 47/36* | (2006.01) | |
| *A61K 47/40* | (2006.01) | |

(56) References Cited

U.S. PATENT DOCUMENTS

| | | | |
|---|---|---|---|
| 5,968,544 A | 10/1999 | Howard et al. | |
| 6,114,379 A * | 9/2000 | Wheelwright | A61P 3/02 |
| | | | 514/492 |
| 7,432,073 B2 | 10/2008 | Niwa et al. | |
| 2001/0042936 A1 | 11/2001 | Kessel et al. | |
| 2004/0013732 A1 | 1/2004 | Farber et al. | |
| 2006/0151899 A1* | 7/2006 | Kato | A61P 3/00 |
| | | | 264/4.1 |
| 2007/0116836 A1* | 5/2007 | Prakash | A61P 27/02 |
| | | | 426/548 |
| 2008/0020995 A1 | 1/2008 | Purpura et al. | |
| 2010/0055178 A1 | 3/2010 | Vilallobos | |
| 2011/0251280 A1 | 10/2011 | Owoc | |
| 2014/0066512 A1* | 3/2014 | O'Gorman | A23L 29/238 |
| | | | 514/565 |
| 2014/0105994 A1 | 4/2014 | Wu et al. | |
| 2015/0238453 A1 | 8/2015 | Owoc | |
| 2016/0120817 A1 | 5/2016 | Doherty | |

FOREIGN PATENT DOCUMENTS

| | | |
|---|---|---|
| CN | 103404854 A | 11/2013 |
| CN | 104432095 A | 3/2015 |
| CN | 105285159 B | 8/2020 |
| KR | 20080068671 A | 7/2008 |
| KR | 20100024657 A | 3/2010 |
| WO | 2003026439 A1 | 4/2003 |

OTHER PUBLICATIONS

Bird, S, "Creatine supplementation and exercise performance: a brief review", Journal of Sports Science and Medicine 2, 123-132 (2003).

Database, "Aseptic Drink Packages", Database accession No. 10086250, MINTEL, 2 pages (2001).

Patent Cooperation Treaty, International Search Report and Written Opinion for PCT/US2018/056591, 8 pages, dated Dec. 21, 2018.

Alam, M, et al., "FDA-Approved Natural Polymers for Fast Dissolving Tablets", Journal of Pharmaceutics, Article ID 952970, 6 pages (2014).

Davis, M, et al., "Recent strategies in spray drying for the enhanced bioavailability of poorly water-soluble drugs", Journal of Controlled Release 269, 110-127 (2018).

Debnath, S, et al., "A Review on Natural Binders used in Pharmacy", Asian Journal of Pharmaceutical Research 9 (1), 55-60 (2019).

Incredible Egg, "Emulsification—American Egg Board", https://www.incredibleegg.org/professionals/manufacturers/real-egg-functionality/emulsification, 3 pages, (2023).

Kelleher, J, et al., "A comparative study between hot-melt extrusion and spray-drying for the manufacture of anti-hypertension compatible monolithic fixed-dose combination products", International Journal of Pharmaceutics 545, 183-196 (2018).

Maniruzzaman, M, et al., "Hot-Melt Extrusion (HME): From Process to Pharmaceutical Applications", Recent Advances in Novel Drug Carrier Systems, Chapter 1, 15 pages, http://dx.doi.org/10.5772/51582 (2012).

Mohammed, N, et al., "Spray Drying for the Encapsulation of Oils—A Review", Molecules 25, 3873, 16 pages, doi:10.3390/molecules 25173873 (2020).

Ordoubadi, M, et al., "Mechanistic Formulation Design of Spray-Dried Powders", KONA Powder and Particle Journal No. 40, 149-171 (2023).

Patil, H, et al., "Hot-Melt Extrusion: from Theory to Application in Pharmaceutical Formulation", AAPS PharmSciTech 17 (1), 20-42 (2015).

Pharma Excipients, "Advantages and Disadvantages of Hot Melt Coating", https://www.pharmaexcipients.com/coating/advantages-hot-melt-coating, 6 pages (2023).

Reno, C, et al., "Preparation and properties of α-tricalcium phosphate microspheres by spray drying", Ceramica 65, 599-604 (2019).

Sandhu, H, et al., "Overview of Amorphous Solid Dispersion Technologies", Advances in Delivery Science and Technology, DOI 10.1007/978-1-4939-1598-9_3, 91-122 (2014).

Singh, A, et al., "Characterizing the pH-Dependent Release Kinetics of Food-Grade Spray Drying Encapsulated Iron Microcapsules for Food Fortification", Food Bioprocess Technol 11, 435-446 (2018).

Sosnik, A, et al., "Advantages and challenges of the spray-drying technology for the production of pure drug particles and drug-loaded polymeric carriers", Advances in Colloid and Interface Science 223, 40-54 (2015).

Moura, F, et al., "Characterization and physicochemical properties of pectins extracted from agroindustrial by-products", J Food Sci Technol 54 (10), 3111-3117 (2017).

Yin, et al., "Influence of Pea Protein Aggregates on the Structure and Stability of Pea Protein/Soybean Polysaccharide Complex Emulsions", Molecules 20, 5165-5183 (2015).

Brummer, et al., "Structural and functional characteristics of dietary fibre in beans, lentils, peas and chickpeas", Food Research International 67, 117-125 (2015).

Libretexts, "Carbohydrates", General Biology 1e (OpenStax), Unit I, Section 3.2, https://bio.libretexts.org/@go/page/1789, 12pgs (access date: Jun. 24, 2025).

Wittkowski, K, "The Effect of Alpha-Cyclodextrin on Postprandial Glucose Excursions: a Systematic Meta-Analysis", Cureus vol. 14(11): e31160, 11 pgs (2002).

* cited by examiner

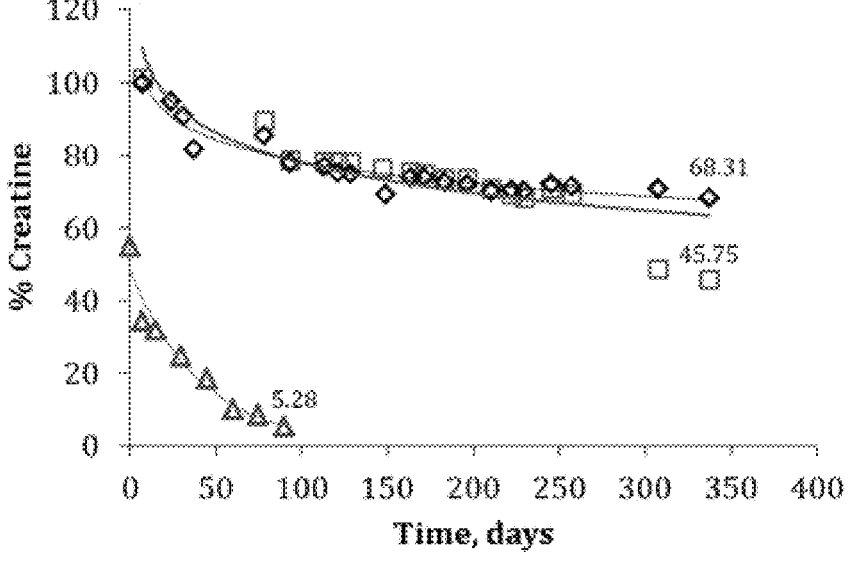

SHELF-STABLE NITROGENOUS ORGANIC ACID COMPOSITIONS

FIELD OF THE INVENTION

The present invention relates to compositions and methods for increasing nitrogenous organic acid solubility and stability. More specifically, the invention relates to methods for formulating products comprising creatine in a more soluble form with increased shelf stability in water even after high-heat processing, as well as compositions made by such methods.

BACKGROUND OF THE INVENTION

Creatine (N-(aminoiminomethyl)-N-methyl glycine) is a nitrogenous organic acid. About 95% of the creatine in the human body is found in the muscle tissue. Because creatine plays a significant role in muscle metabolism, it is a popular supplement for athletes. It has also been suggested to have beneficial effects for disease conditions such as heart disease, chronic obstructive pulmonary disease (COPD), and Parkinson's disease.

Creatine has become one of the most popular and widely used supplements in the sports nutrition market, with athletes often consuming loading doses as high as 20-30 g/day for 5-7 days. Reported annual sales of creatine supplements in the U.S. alone increased from $50 million in 1996 to over $400 million in 2001 (Bird, Stephen P., Creatine Supplementation and Exercise Performance: A Brief Review, *Journal of Sports Science and Medicine* (2003) 2, 123-132).

In its solid form, creatine monohydrate powder is very stable, showing no signs of degradation over years, even at elevated temperatures. However, its use in liquid products such as sports nutrition drinks, for example, has been limited by its low solubility and its decreased stability in solution. Although creatine solubility may be increased at lower pH and higher temperatures (lower pH being common in drink formulations and higher temperatures being used for processing and packaging those products), under those conditions it also rapidly degrades by self-cyclizing into creatinine.

One attempt to solve this problem has been described in U.S. Patent Publication Number 2011/0251280A1 (Owoc, J.), which discloses the synthesis of amide-protected creatine molecules, generally formed by synthesizing peptides such as creatyl-L-glutamine, or creatyl-L-leucine. However, Owoc also suggests that "[p]referably, the composition comprises acid stable protein isolates, or a combination or blend of protein isolates, concentrates and hydrolyzates and caseins in micellar forms, a suitable aqueous solvent or vehicle, a non-aqueous vehicle, a preservative, a physical stabilizing ingredient, one or more surfactants, and/or one or more buffer salts that can render the composition pH stable. Another option is disclosed in US 2016/0120817A1 (Doherty, S.) as a process for producing microcapsules comprising creatine encapsulated and stabilized within a whey protein shell. Doherty notes that the formulation should not only be stable in liquid, but also be readily absorbed in the digestive system. Owoc discloses in US20150238453A1 an alternative approach for addressing that concern, since, as Owoc observed in paragraph [0019], "[i]t is well known that chain length has an effect on the absorption of biologically active peptides from the GI tract. Furthermore, we know that the potency of orally consumed peptides decreases as the chain length increases." In Owoc's alternate approach, he creates N-acetyl or N-acyl creatine, wherein an acetyl or acyl group replaces an active hydrogen of the amino group in creatine, and creatyl peptides wherein an amino acid is bonded to acetylated or acylated creatine.

Emulsions comprising creatine and medium chain triglycerides (MCTs) have been described, but the oil, at some point of storage, becomes oxidized and can become rancid.

Powdered drink mix sales have reached approximately one billion dollars per year. Their attractiveness is due, in part, because they can be available to consumers in canister-type containers, in single-shot sleeves, often referred to as "sticks," in cap-mounted delivery systems, or in tablet form, for example. In these forms, the mixes may be carried by the consumer in a pocket, purse, gym bag, briefcase, or lunchbox. Creatine has typically not been a suitable ingredient for many of these products because it is very unstable in water and not sufficiently soluble to be readily mixed to form a solution from a powder mix. Therefore, what are needed are compositions and methods for providing creatine in a form that increases both its solubility and stability. Also needed are compositions and methods for providing creatine in formulations that do not undergo significant creatine degradation over shelf time, as well as compositions that provide creatine in a form that will not settle/recrystallize, agglomerate, or otherwise create a potential choking hazard in a product such as a beverage.

SUMMARY OF THE INVENTION

The invention relates to a method for making a more shelf-stable form of at least one nitrogenous organic acid, the method comprising the steps of combining lecithin, water, and at least one polysaccharide to form a surfactant solution; admixing at least one nitrogenous organic acid with the surfactant solution to form a dispersion; and homogenizing the dispersion to produce a nitrogenous organic acid colloidal dispersion. In some embodiments of the invention, the at least one polysaccharide is selected from the group consisting of polysaccharides with a dextrose equivalent (DE) value of from about 4.0 to about 12.0, polysaccharides with a bound galacturonic acid value of less than about 8 g/100 g, and combinations thereof. In embodiments of the invention applied to neutral beverage applications, the at least one polysaccharide can be selected from the group consisting of polysaccharides with a dextrose equivalent (DE) value of from about 4.0 to about 12.0, polysaccharides with a bound galacturonic acid value of less than about 8 g/100 g, and combinations thereof. In embodiments of the invention for use in high-acid beverage applications, the at least one polysaccharide has a bound galacturonic acid value of at least about 8 g/100 g. The method optionally comprises a step of drying the nitrogenous organic acid colloidal dispersion. In various embodiments, the step of drying is performed by spray-drying. The invention also relates to products made by this method.

In various embodiments of the invention, the at least one nitrogenous organic acid is creatine, and in various embodiments the form of creatine may be chosen from among the group consisting of creatine monohydrate, creatine hydrochloride, buffered creatine, creatine magnesium chelate, di-creatine malate, creatine-magnesium chelate, creatine alpha-amino-N-butyrate, and combinations thereof. In various embodiments of the invention, the lecithin can be soy lecithin. In various embodiments, the polysaccharide is selected from the group consisting of gum acacia, gum Arabic, chitosan sulfate, maltodextrin, pectin, alginate and combinations thereof. In various embodiments of the invention, alpha cyclodextrin is optionally admixed with the creatine and the surfactant solution to form the dispersion.

In various aspects of the invention, the polysaccharide is maltodextrin, and in various aspects of the invention the ratio of lecithin to maltodextrin comprises from about 0.7 to about 1.0 Lecithin/Maltodextrin. In various aspects of the invention, the creatine dispersion is homogenized at pressures of from about 500 to about 3000 psi. In various aspects, the homogenization pressure is about 500 psi (or 34 bar), and in various aspects the ratio of lecithin to polysaccharide to creatine is, for example, from about 1:1:2 to about 1:1:12, from about 1:1:2 to about 1:1:12, from about 1:1:2 to about 1:1:2.5, and in some specific instances, about 1:1:6.

BRIEF DESCRIPTION OF THE DRAWINGS

FIG. 1 is a graph illustrating the comparison between creatine stability for a product of the invention and for a second product, an emulsion comprising creatine and formed using medium chain triglycerides (MCTs). Creatine stability measurements were performed over a period of eleven (11) months, two (2) days. For creatine monohydrate, pH 7.0 (Δ), $y=48.294e^{-.0024x}$, $R^2=0.9804$. For encapsulated creatine formula 1, pH 7.0 (□), $y=-11.96 \ln(x)+132.94$, $R^2=0.69$. For encapsulated creatine formula 2, pH 7.1 (◇), $y=-8.709 \ln(x)+118.29$, $R^2=0.9191$.

DETAILED DESCRIPTION

The inventors have discovered that a stable creatine composition, which can be in liquid or dry form for use as an ingredient in products such as beverages and nutritional bars, for example, can be made using a straightforward method using a limited number of ingredients, all being generally recognized as safe (GRAS), thereby eliminating the need for numerous ingredients and/or chemical reactions to modify creatine to enhance its storage stability and bioavailability. The invention relates to a method for making a colloidal dispersion of at least one nitrogenous organic acid (e.g., creatine), the method comprising the steps of combining lecithin, water, and at least one polysaccharide to form a surfactant solution; admixing at least one nitrogenous organic acid (e.g., creatine monohydrate) with the surfactant solution to form a dispersion (e.g., a creatine dispersion); and homogenizing the dispersion to produce a nitrogenous organic acid colloidal dispersion (e.g., a colloidal dispersion comprising creatine). In some embodiments of the invention, the at least one polysaccharide is selected from the group consisting of polysaccharides having a dextrose equivalent (DE) value of from about 4.0 to about 12.0, polysaccharides having a bound galacturonic acid value of less than about 8 g/100 g, and combinations thereof. In embodiments of the invention applied to neutral beverage applications, the at least one polysaccharide will preferably be selected from the group consisting of polysaccharides having a dextrose equivalent (DE) value of from about 4.0 to about 12.0, polysaccharides having a bound galacturonic acid value of less than about 8 g/100 g, and combinations thereof. In embodiments of the invention for use in high-acid beverage applications, the at least one polysaccharide will preferably have a bound galacturonic acid value of at least about 8 g/100 g. The method optionally comprises the step of drying the nitrogenous organic acid colloidal dispersion. In various embodiments, the step of drying is performed by spray-drying. The invention also relates to products made by this method.

"Surfactants" are organic molecules which decrease the surface tension between two liquids or between a liquid and a solid. As used herein, the term "surfactants" is used for agents that decrease the surface tension between a liquid and solid phase. For example, the solid phase can be creatine monohydrate powder, which generally is insoluble, or has very low solubility, in water. The phrase "as in dispersion" indicates the concentration of an ingredient in the colloidal dispersion, before being dried into powder. A "colloidal dispersion" is a system in which particles of colloidal size (e.g., about 1 nm to about 1 μm) are dispersed in a continuous phase of a different composition. The phrase "as in powder" indicates the concentration of an ingredient in the dried (e.g., spray-dried) powder.

Homogenization can be performed by methods known to those of skill in the art, and those of skill in the art will recognize that homogenization is generally performed until a substantially homogenized state is produced (i.e., a state in which the composition is homogenized as much as is readily achievable under normal processing conditions by the homogenization method selected). The combination of ingredients used to prepare the inventive composition can be formulated at lower homogenization pressures commonly used during commercial processing (i.e. 500-2500 psi), while providing excellent creatine stability for at least about 8-12 months. (Generally, previously-described methods for preparing emulsions of various ingredients have required higher shear of 5000-6000 psi to attain suitable particle size and colloidal stability to produce a colloidal dispersion.) The method of the invention also increases the percentage of creatine in the dispersion before and after spray drying, for maximum powder recovery after a single spray-dry run.

Very few food-grade encapsulating agents withstand high temperature processing, such as ultra-high temperature (UHT) or Hot Fill processing, at such high solids levels in a slurry. However, the selected polysaccharides, such as maltodextrin, provide effective encapsulating agents when used in the method of the invention, which may, in various embodiments of the invention, be substituted with, or combined with, one or more other food-grade ingredients such as gum acacia, gum Arabic, chitosan sulfate, pectin, alginate, combinations thereof, or other polysaccharides which may be chosen by one of skill in the art, given the information provided in the present disclosure. Polysaccharide(s) with either a dextrose equivalent (DE) value of from about 4.0 to about 12.0, or bound galacturonic acid value of less than about 8 g/100 g, can be used for neutral beverage applications. Polysaccharide(s) used in high-acid beverage applications will preferably have a bound galacturonic acid value of at least about 8 g/100 g.

Galacturonic acid (D-galacturonic acid) is an oxidized form of D-galactose. Pectin, for example, consists primarily of polymeric galacturonic acid (polygalacturonic acid). Galacturonic acid has an aldehyde group at C1 and a carboxylic acid group at C6. Galacturonic acid monomers that form part of a long chain polysaccharide are referred to as bound galacturonic acid units. The minimum value of bound galacturonic acid for identifying polysaccharides for use in the method of the invention has been determined by the inventor, through multiple experiments using different polysaccharides having different bound galacturonic acid values. It is known that the higher the surface charge on an encapsulated microstructure, the higher is its stability. (Yin, Baoru, Influence of Pea Protein Aggregates on the Structure and Stability of Pea Protein/Soybean Polysaccharide Complex Emulsions, *Molecules* (2015) 20, 5165-5183.) In the method of the present invention, because galacturonic acid has carboxylic acid groups, they tend to electrostatically enhance colloidal stability at pH values greater than its isoelectric point. At these pH values it has high negative charge due to ionization of carboxylic acid groups of the galacturonic acid moiety (Yokoyama A., Stabilization mechanism of colloidal suspensions by gum tragacanth: The influence of pH on stability, *Journal of Colloid and Interface Science* (1988) 126(1), 141-149). For high-acid beverage applications, the ionized carboxylic acid groups of the galacturonic acid moieties of the polysaccharide(s) complex with the positively-charged choline heads of lecithin (e.g., soy lecithin), thus making the microencapsulation more impermeable and colloidally stable—protecting the low pH and thermo-labile bioactive agents encapsulated within the compact micro-structure.

In various embodiments of the invention, the at least one nitrogenous organic acid is creatine. In various embodiments of the invention, the lecithin is soy lecithin. In various embodiments of the invention, alpha cyclodextrin is optionally admixed with the creatine and the surfactant solution.

In various aspects of the invention where maltodextrin is the selected polysaccharide, the ratio of lecithin to maltodextrin comprises from about 0.7 to about 1.0 Lecithin/Maltodextrin. Examples of the ratio of lecithin to polysaccharide to creatine are from about 1:1:2 to about 1:1:12, from about 1:1:2 to about 1:1:12, from about 1:1:2 to about 1:1:2.5, or even more specifically, in some formulations about 1:1:6, the ratios for specific formulations being readily determined, given the information provided herein by the inventors, by those of skill in the art without undue experimentation. In various aspects of the invention, the creatine dispersion is homogenized at a pressure of from about 500 to about 3000 psi. In various aspects, the homogenization pressure is about 500 psi/34 bar.

The inventive creatine compositions can be particularly useful for those for whom higher-dose creatine supplementation may be beneficial, such as athletes. However, the benefits of creatine appear to be many and varied, leading to proposals for its use as a supplement for use by individuals with diseases affecting the neuromuscular system, such as muscular dystrophy (MD), in aging populations for wasting syndromes, muscle atrophy, fatigue, gyrate atrophy, Parkinson's disease, Huntington's disease and other brain pathologies, and in individuals who have high cholesterol (creatine having been shown to reduce cholesterol by up to 15%). Some have suggested that creatine may also increase growth hormone production. For many of these individuals, powders which may be successfully admixed into water, milk, fruit juice, or another type of beverage, or bottled or canned beverages, may provide a significantly better option for creatine administration than would other options such as, for example, ingestion of capsules. Creatine has been suggested to be more bioavailable if it is ingested in conjunction with both protein and carbohydrate, and drinks or drink mixes provide good options for accomplishing that goal. Powdered drink mixes can provide creatine supplementation in a very convenient form, as they can be packaged in small or large canister-type containers, zippered pouches, pouches with screw-top caps, and/or in single-shot sleeves ("sticks," or "slim-sticks"), for example. In these forms, the mixes may be carried by the consumer in a pocket, purse, gym bag, briefcase, or lunchbox.

In the method for making a more shelf-stable creatine composition, a solution of surfactants is made. In various embodiments, the "surfactants" comprise soy lecithin, and maltodextrin. Creatine monohydrate is added to the surfactant solution. A typical creatine concentration could be, for example, 23.7 g/100 g as in dispersion or 65.2 g/100 g as in powder. Where creatine monohydrate is used as the source of creatine, it may, for example, be incorporated at from about 15.5 to 23.7 g/100 g as in dispersion or 56.4 to 65.2 g/100 g as in powder. Lecithin may be incorporated at up to about 7.7 g/100 g as in dispersion or 20.3 g/100 g as in powder. Alpha cyclodextrin can also be optionally added to enhance the effect on the performance of the formulation with regards to creatine shelf stability. This mixture is processed through a homogenizer at, for example, 500 psi/34 bar, 1 pass. The dispersion thus formed is then spray-dried ($T_{Inlet}$=200° C. and $T_{Outlet}$=100° C., for example). Without being bound by theory, where lecithin, cyclodextrin, and maltodextrin are used in combination, the inventors believe that since creatine is almost hydrophobic, it is encapsulated by soy lecithin and cyclodextrin as the surfactants, with the maltodextrin (e.g., MD040) forming an additional wall material that surrounds the other ingredients. A product formed by this method can, for example, be produced to provide about 61.2 grams of creatine per 100 grams of spray-dried powder. That is, the method produces a creatine encapsulation efficiency of about 95% (based on the expected creatine levels of ~65 g in 100 g of spray dried powder).

Products made by the method of the invention can be successfully processed using ultra-high temperature processing (UHT) for neutral beverages, and hot-fill processing for high-acid beverages, which are often used to kill bacteria and extend shelf life of liquids, providing a significant advantage as compared to the processing limits associated with products such as emulsions formed using ingredients such as medium-chain triglycerides.

Creatine compositions according to the invention may be formulated using various forms of creatine, including, for example, creatine monohydrate, creatine hydrochloride, buffered creatine, creatine magnesium chelate, di-creatine malate, creatine-magnesium chelate, creatine alpha-amino-N-butyrate. Some of these, and other, creatine analogs have been developed to improve the solubility of creatine. However, when incorporated into products of the present invention, these analogs can also be provided in a form that significantly decreases the rate of creatine degradation in water, increases its shelf-life stability, and significantly improves stability under ultra-high temperature (UHT) or hot-fill processing. Creatine compositions made by the method of the invention may also comprise additional ingredients such as branched-chain amino acids (BCAAs), for example.

Products of the invention include bottled and/or canned colloidal dispersions made by the method of the invention, with added flavors, coloring, etc., as desired, and/or powdered drink mixes made by spraying (e.g., spray-drying) one or more colloidal dispersions, the powdered mix being especially suited for mixing with water at or about neutral pH. The invention also provides creatine in a form that can be used in "dry," semi-moist, and moist food products, such as nutritional bars, for example, increasing the shelf stability of the creatine in those products. Uzzan et al. reported that water activity affects creatine stability. "Water activity" (aw) refers to water in food which is not bound to food molecules, but it is not the same thing as moisture content. Foods may have the same moisture content and yet have quite different water activities. Bread, for example, can have a water activity of about 0.95. In the Uzzan study the highest water activity (0.983) reduced the half-life of creatine to 43 days, while at the lowest water activity (0.31) the half-life of creatine was 182 days. (Uzzan, Michael, Nechrebeki, Jacob, Zhou, Peng and Labuza, Theodore P. (2009), "Effect of water activity and temperature on the stability of creatine during storage," *Drug Development and Industrial Pharmacy*, 35:8, 1003-1008.) The method of the invention provides creatine in a form that is more protected from the effects of water in the environment surrounding the creatine, which provides a distinct advantage for the formulation of aqueous-based products, as well as dry, semi-moist and moist products which may have a higher water activity that would generally reduce the half-life of isolated creatine in the products into which it is incorporated. Such products can include a variety of products formulated for human and/or animal consumption, such as breakfast bars, protein bars, dog or cat foods and/or treats, etc.

The invention has been described as "comprising" certain steps and ingredients, which those of skill in the art may also "consist of" or "consist essentially of" those steps and/or ingredients. Therefore, where the term "comprising" is used and the invention is intended to be more narrowly defined, the terms "consisting of" or "consisting essentially of" may also be used to describe the invention. The invention may also be further described by means of the following non-limiting examples.

EXAMPLES

Neutral pH Beverage Application

A solution of surfactants was made by combining soy lecithin with 48-98% acetone insolubility (3.1 to 9.9 g/100 g as in dispersion or 9.2 to 16.9 g/100 g as in powder) in water (pH 7.0), with maltodextrin MD040 (Maltrin®, Grain Processing Corporation, 4.9-10.2 g/100 g as in dispersion or 12.4-17.7 g/100 g as in powder). Then the micronized (200 Mesh size or 70-80 μm) creatine monohydrate (23.7-40.2 g/100 g as in dispersion or 65.2-79.3 g/100 g as in powder), along with Alpha cyclodextrin (Cavamax®, Wacker Chemie AG, 0-0.26 g/100 g as in dispersion or 0-0.4 g/100 g as in powder), was added to the above solution of surfactants. Ingredient concentrations for the final composition are listed in Table 1. After premixing the dispersion, it was run through the homogenizer at 500 psi/34 bar, 1 pass. The dispersion thus formed was heated to a pasteurization temperature of 72° C., for 30 min. Finally, this dispersion was spray dried, with $T_{Inlet}$=220-230° C. and $T_{Outlet}$=92-100° C. The concentration of ingredients in the spray-dried powder of final composition is shown in Table 2. Creatine shelf stability was evaluated at pH 3.3-7.0.

TABLE 1

| Net Concentration of Ingredients in Colloidal Dispersion (g/100 g Dispersion) for Neutral Beverage Application | |
|---|---|
| Soy Lecithin, g/100 g | 9.94 |
| Cavamax ® (α-CD), g/100 g | 0.26 |
| Wt of Creatine (g) per 100 mL drink | 25.35 |
| Maltrin ® MD040 Maltodextrin, g/100 g | 10.2 |

TABLE 2

| Net Concentration of Ingredients in Spray dried Powder (g/100 g Powder) for Neutral Beverage Application | |
|---|---|
| Soy Lecithin, g/100 g | 16.21 |
| Cavamax ® (α-CD), g/100 g | 0.42 |
| Wt of Creatine (g) per 100 mL drink | 66.7 |
| Maltrin ® MD040 Maltodextrin, g/100 g | 16.67 |

8

Acidic Beverage Application

For the high-acid application, the formulation was similar to that of the neutral pH application formulation described above, except that maltodextrin was replaced with polysaccharide with a bound galacturonic acid value of at least 8 g/100 g. Also, an amount of salt, $Ca^{2+}$ or $Mg^{2+}$, was added (0.4 to 0.74 g/100 g as in dispersion or 0.9 to 1.3 g/100 g as in powder) to enhance the flow property of spray-dried powder. Initially, polysaccharide along with $Ca^{2+}$ or $Mg^{2+}$ salts were dispersed in hot water (50-55° C.), and then other ingredients were added in the following order: soy lecithin, Alpha-cyclodextrin, and micronized creatine monohydrate. This formulation was repeated, using different polysaccharides having different bound galacturonic acid values of at least 8 g/100 g.

Spray-dried powder was analyzed to determine the amount of creatine (g) in 100 g of spray dried powder. This value was compared with a theoretical amount of creatine in spray-dried powder, indicating that there was a ~95-100% creatine encapsulation, based on the expected creatine levels of ~65-75 g in 100 g of spray-dried powder.

Shelf-Stability of Creatine

For the creatine shelf-stability study, the corresponding spray-dried powders produced from the slurry were used for determining the chemical stability of creatine monohydrate either in a neutral pH (6.8-7.0) drink or an acidic pH (3.3-3.7) drink formula. For this determination, the creatine-containing beverages were prepared at their respective pH, using spray-dried powder. They were then bottled using either UHT conditions for neutral beverage applications or through hot-fill process conditions for acidic pH beverage applications. These bottles were stored at an ambient temperature of 22-25° C. Then the chemical stability of creatine was checked in these bottles at time intervals of days, using the HPLC-UV method for creatine and creatinine detection. The encapsulated creatine shelf-stability of neutral beverage final formulas indicated ~67% of creatine levels after 12 months shelf storage after UHT processing, having a degradation curve of: y=–8.709 ln(x)+118.29 (y=% creatine levels, after (x) number of days). This shelf stability curve was compared with another encapsulated creatine formula, and with non-encapsulated creatine monohydrate. A comparison of creatine shelf-stability in non-encapsulated creatine monohydrate and encapsulated formulas at neutral pH conditions is shown in FIG. 1. At acidic pH conditions, the creatine stability increased (i.e. creatine levels stayed higher), when polysaccharides with higher bound galacturonic acid levels were used in the formula. The relationship curve for bound galacturonic acid (g/100 g) in polysaccharide, versus percentage creatine levels after 10 days of shelf stability was found to be, y=41.295x$^{0.2753}$ (y=bound galacturonic acid (g/100 g), x=% creatine levels after 10 days of shelf stability), which was determined and confirmed after repeated trials.

What is claimed is:

1. A method for making a shelf-stable encapsulated creatine monohydrate colloidal dispersion composition the method comprising the steps of combining starting materials comprising lecithin, water, at least one polysaccharide, and, optionally, calcium chloride to form a surfactant solution; admixing creatine monohydrate with the surfactant solution to form a dispersion; homogenizing the dispersion; and spray-drying the dispersion to produce the encapsulated creatine monohydrate colloidal dispersion composition; wherein the at least one polysaccharide comprises a non-pectin polysaccharide; wherein the at least one polysaccharide has a bound galacturonic acid value of at least about 8 g/100 g; wherein the method produces a creatine monohydrate encapsulation efficiency of about 95%; wherein the creatine monohydrate has a net concentration of 23.7-40.2 g/100 g as in dispersion; wherein the lecithin has a net concentration of 3.1-9.9 g/100 g as in dispersion; and wherein the at least one polysaccharide has a net concentration of 4.9-10.2 g/100 g as in dispersion.

2. The method of claim 1 wherein the lecithin is soy lecithin.

3. The method of claim 1 wherein the ratio of lecithin to polysaccharide comprises from about 0.7 to about 1.0.

4. The method of claim 1 wherein the creatine monohydrate colloidal dispersion is homogenized at a homogenization pressure from about 500 to about 3000 psi.

5. The method of claim 4 wherein the homogenization pressure is about 500 psi/34 bar.

6. The method of claim 1 wherein the spray-drying temperatures are $T_{inlet}$=220-230° C. and $T_{outlet}$=92-100° C.

7. The method of claim 1, wherein the creatine monohydrate comprises solid phase nitrogenous organic acid creatine monohydrate.

8. The method of claim 1, wherein the creatine monohydrate has a particle size of less than 80 μm.

9. The method of claim 1, wherein the encapsulated creatine monohydrate colloidal dispersion composition is soluble in liquid.

10. The method of claim 1, further comprising the step of pasteurizing the dispersion.

11. A method for making a shelf-stable encapsulated creatine monohydrate colloidal dispersion composition, the method comprising the steps of combining lecithin, water, and at least one polysaccharide with a bound galacturonic acid value of less than about 8 g/100 g to form a surfactant solution; admixing nitrogenous organic acid creatine monohydrate with a particle size of less than 80 μm with the surfactant solution to form a dispersion; homogenizing the dispersion; and spray-drying the dispersion to produce the encapsulated nitrogenous organic acid creatine monohydrate colloidal dispersion composition; wherein the polysaccharide is selected from the group consisting of maltodextrin, alpha cyclodextrin, and combinations thereof; wherein the encapsulated creatine monohydrate colloidal dispersion composition has a chemical stability of about 67% after 12 months at a neutral pH; wherein the creatine monohydrate has a net concentration of 23.7-40.2 g/100 g as in dispersion; wherein the lecithin has a net concentration of 3.1-9.9 g/100 g as in dispersion; and wherein the at least one polysaccharide has a net concentration of 4.9-10.2 g/100 g as in dispersion.

12. The method of claim 11, further comprising the step of pasteurizing the dispersion.

13. A method for making a shelf-stable encapsulated creatine monohydrate colloidal dispersion composition, the method comprising the steps of combining soy lecithin, water, maltodextrin, and alpha cyclodextrin, to form a surfactant solution; admixing creatine monohydrate with the surfactant solution to form a dispersion; pasteurizing the dispersion; homogenizing the dispersion; and spray-drying the dispersion to produce the encapsulated creatine monohydrate colloidal dispersion composition; wherein the method produces a creatine monohydrate encapsulation efficiency of about 95%; wherein the creatine monohydrate has a net concentration of 23.7-40.2 g/100 g as in dispersion; wherein the lecithin has a net concentration of 3.1-9.9 g/100 g as in dispersion; and wherein the at least one polysaccharide has a net concentration of 4.9-10.2 g/100 g as in dispersion.

* * * * *